United States Patent [19]

Shimizu

[11] Patent Number: 4,624,150
[45] Date of Patent: Nov. 25, 1986

[54] SAMPLING PIPE MEANS FOR CONNECTION TO A FLUID ANALYZER

[75] Inventor: Sumio Shimizu, Kyoto, Japan
[73] Assignee: Horiba, Ltd., Kyoto, Japan
[21] Appl. No.: 748,465
[22] Filed: Jun. 25, 1985

[30] Foreign Application Priority Data

Jun. 26, 1984 [JP] Japan .................. 59-132224

[51] Int. Cl.⁴ .......................................... G01N 35/00
[52] U.S. Cl. ................................................ 73/864.81
[58] Field of Search .................. 73/864.81, 27 R; 285/10, 11, 425

[56] References Cited

U.S. PATENT DOCUMENTS 3,976,450  8/1976  Marcote et al. ................ 73/864.81
4,452,277  6/1984  Wells ................................ 285/425

Primary Examiner—Stewart J. Levy
Assistant Examiner—Robert R. Raevis
Attorney, Agent, or Firm—Wenderoth, Lind & Ponack

[57] ABSTRACT

A sampling pipe device for connection to a fluid analyzer mounted in a substantially vibration free condition and having at least one fluid introducing pipe extending therefrom. The sampling pipe device has a pipe connecting block having a number of recesses therein corresponding to the number of fluid introducing pipes on the analyzer, each recess having a diameter larger than the outside diameter of the corresponding fluid introducing pipe and having a sampled fluid introducing opening therein for introducing the sampled fluid into the recess. The pipe connecting block is in a fixed position relative to the analyzer with a fluid introducing pipe in each recess in non-contact relationship to the inside wall of the recess.

4 Claims, 4 Drawing Figures

SAMPLING PIPE MEANS FOR CONNECTION TO A FLUID ANALYZER

BACKGROUND OF THE INVENTION

1. Field of the Invention

The present invention relates to sampling conduits or pipes for introducing fluids such as gas into an analyzer, in particular to sampling pipes suitable for use with "highly sensitive analyzers" which are very susceptible to fluctuation in the flow rate of the sample and to vibration.

2. Description of the Prior Art

Analyzers, the output of which is affected by fluctuation in the flow rate of a sample, require constant flow rate type sampling. Precise instruments, such as a pressure regulator, have heretofore been used in order to attain constant flow rate type sampling. However, instruments of this type are very expensive, and cause fluctuation of the flow rate of a sample therein due to the hysteresis thereof, and in addition, require a choke to reduce the flow rate of a sample when circumstances require.

In addition, analyzers, the output of which is sensitive to mechanical vibrations, must be provided with a means for preventing vibrations. However, although a means for preventing vibrations of the body of an analyzer has heretofore been provided, a means for preventing vibrations transmitted through sampling pipes has not been provided, and sampling pipes have been directly connected to the body of the analyzer. As a result, vibrations are transmitted to the body of the analyzer through the pipes, thereby influencing the output of the analyzer.

Since such highly sensitive analyzers are sensitive to both fluctuation in the sample flow rate and vibrations, the analyzers should be provided both with a means for preventing fluctuation of the flow rate of the sample and a means for preventing vibrations.

SUMMARY OF THE INVENTION

Thus, it is an object of the present invention to provide a novel sampling pipe means suitable for use with highly sensitive analyzers in which both the fluctuation of the sample flow rate and vibrations transmitted to the body of an analyzer through said sampling pipe means can be effectively prevented.

In order to achieve the above described object, the present invention provides a pipe connecting block having a recess having a diameter larger than the outside diameter of the fluid-introducing pipe of the analyzer, said fluid-introducing pipe being fixedly inserted into said opening in noncontact relation with said block.

DESCRIPTION OF THE PREFERRED EMBODIMENTS

Figure 1:
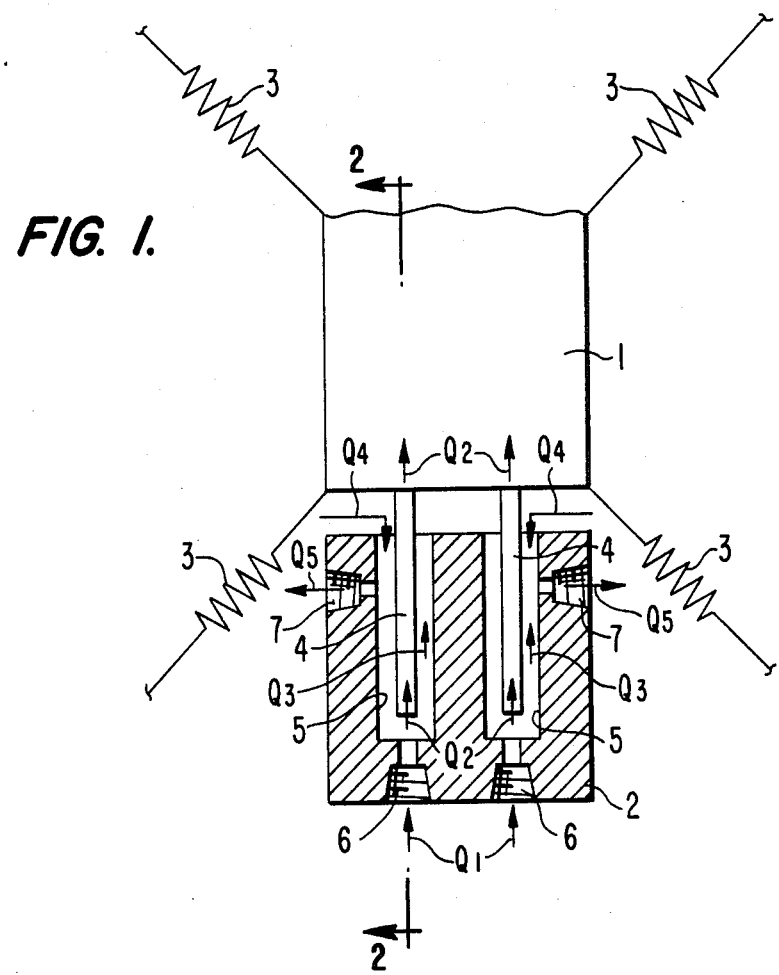
FIG. 1 is a front sectional view showing the principal parts of one embodiment of the sampling pipe means according to the present invention.
Figure 2:
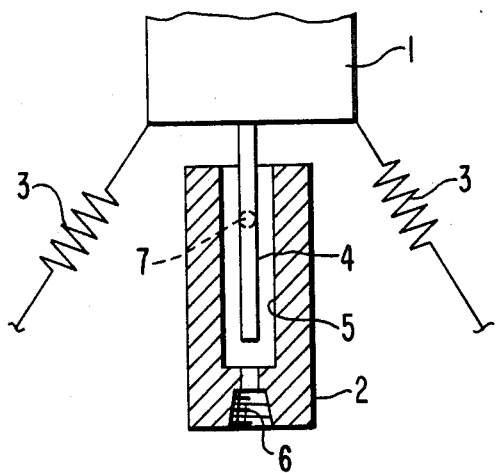
FIG. 2 is a sectional view taken along the line 2—2 of FIG. 1.

Referring now to FIGS. 1 and 2, the body 1 of the analyzer is suspended in vibration free condition in mid-air by means of coiled springs 3. A pipe connecting block 2 is provided in a fixed position relative to said body 1, and has a plurality of recesses 5 having a diameter larger than the outside diameter of a fluid (gas, liquid or the like)-introducing pipes 4 on the body 1 of the analyzer. The fluid-introducing pipes 4 are inserted into said recesses 5 in non-contact relation with said pipe connecting block 2. The fluid-introducing pipes 4 are not in contact with any portion of the inside surface of the corresponding recesses 5 around the circumferential surfaces and the end surfaces thereof. Each recess 5 in said pipe connecting block 2 has an inlet 6 for fluids such as sample gas opening thereinto. In addition, a by-pass outlet 7 is provided just inside the interior of the recess 5.

A suction apparatus (not shown) is connected with the by-pass outlet (7) through a piping. The free end of the fluid-introducing pipe 4 of said body 1 of the analyzer is inserted into said recess 5 so as to be disposed between the inner end of said recess 5 and said by-pass outlet 7 as shown in FIGS. 1 and 2. In addition, although the diameter of each said recess 5 should be larger than the outside diameter of the corresponding fluid-introducing pipe 4, it is not limited to any specific value. In general, it is preferably determined as follows:

The diameter of each recess 5 is such as to minimize the pressure loss resulting from an overflow rate $Q_3$ given by the following equation:

$$Q_1 - Q_2 = Q_3$$

, wherein $Q_1$ designates the flow rate of a fluid introduced through said inlet 6 and $Q_2$ designates the flow rate of a fluid sucked into the body 1 of the analyzer through the corresponding fluid-introducing pipe 4 by a suction means (not shown) forming part of the analyzer 1.

According to the above described construction, since each fluid-introducing pipe 4 on the body 1 of the analyzer is inserted into a recess 5 in said pipe connecting block 2 in noncontact relation, vibrations can almost completely be prevented from being transmitted to the body of the analyzer through the sampling pipe means, and simultaneously, fluctuation of the sample flow rate can be prevented since the part $Q_2$ of the flow rate $Q_1$ of a sample gas introduced through said inlet 6 which is sent to said body 1 of analyzer is kept constant by means of the suction device while the rest, $Q_3 (=Q_1-Q_2)$, is caused to overflow through said recess 5, whereby $Q_3$ fluctuates with the fluctuation of $Q_1$ and therefore a constant quantity $Q_2$ of sample gas is always supplied to the body 1 of the analyzer. As a result, the output of the analyzer is substantially free of the influence of fluctuation of the sample gas flow rate. A gas is sucked through the by-pass outlet (7) at a flow rate of $Q_5 (=Q_3+Q_4)$ in order to prevent the overflown portion from discharging into the outside, wherein $Q_4$ designates a quantity of an air flown from the open end side of the recess 5 into the recess 5, as shown in FIG. 1.

In addition, since the overflow is through the recess (5) ($Q_3>0$), air is prevented from flowing into said fluid-introducing pipe 4 through the recess 5. Accordingly, air can be prevented from flowing into the body of the analyzer together with the sample and having an influence upon the output of the analyzer. Where the sample gas contains noxious gases, noxious gases can be prevented from being discharged into the air by letting them escape through said by-pass outlet 7, as described above.

Figure 3:
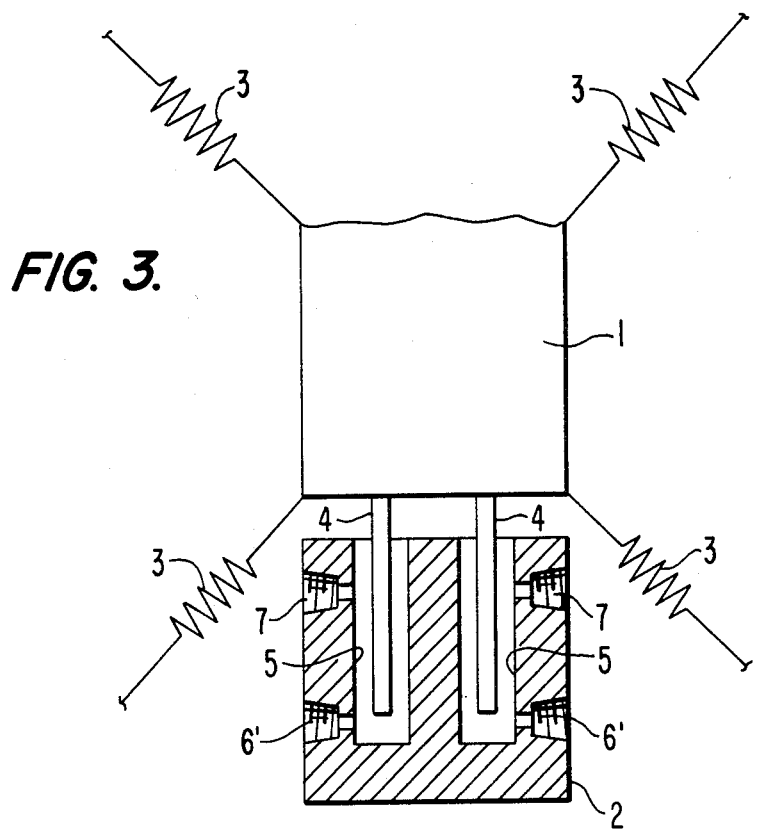
FIGS. 3 and 4 are sectional views showing other embodiments of sampling pipe means according to the present invention.

As an alternative embodiment, the inlet for sampled fluids can be provided in the side wall of said pipe connecting block and opening with each recess 5 as shown in 6' in FIG. 3.

Figure 4:
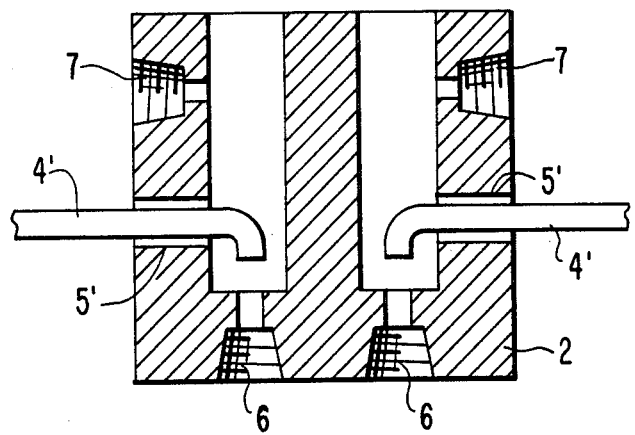

As a further alternative, an opening 5' can be provided in the pipe connecting block into each recess 5, and a fluid-introducing pipe 4' from the analyzer body 1 (not shown) can be inserted into each opening 5' in noncontact relation, the end portion of each fluid-introducing pipe 4' being parallel with the axis of the opening 5', as shown in FIG. 4.

A sampling pipe means having the above described construction according to the present invention has the following advantages:

(1) Since the fluid-introducing pipe 4 is inserted in non-contact relation into the recess 5 in the pipe connecting block 2, vibration can be prevented from being transmitted through the pipe, whereby the influence of the vibration upon the ouput of an analyzer can be substantially reduced in comparison with conventional analyzers.

(2) Since a constant flow rate can be achieved due to the construction in which a fluid-introducing pipe 4 is inserted into the recess 5 in the pipe connecting block 2 as described above, the influence of the fluctuation in the sample gas flow rate upon the output of the analyzer can be reduced, and simultaneously, expensive instruments such as a pressure regulator are not required, whereby an inexpensive analyzer can be provided.

(3) Since a very simple construction in which the fluid-introducing pipe 4 is introduced into a recess 5 in noncontact relation thereto is used, the analyzer is not subject to clogging or troubles other than clogging.

What is claimed is:

1. A sampling pipe means for connection to a fluid analyzer mounted in a substantially vibration free condition and having at least one fluid introducing pipe extending therefrom, said means comprising:

a pipe connecting block having a number of recesses therein corresponding to the number of fluid introducing pipes on the analyzer, each recess having a diameter larger than the outside diameter of the corresponding fluid introducing pipe and having a sampled fluid introducing opening therein for introducing the sampled fluid into said recess, said pipe connecting block being in a fixed position relative to said analyzer with a fluid introducing pipe in each recess in non-contact relationship to the inside wall of the recess and said pipe connecting block further having a bypass outlet opening out of each of said recesses between the free end of the fluid introducing pipe and the mouth of the recess for withdrawing fluid from said recess in excess of that taken into the analyzer through the fluid introducing pipe.

2. A sampling pipe means as claimed in claim 1 in which said sampled fluid introducing opening is in the bottom of the recess.

3. A sampling pipe means as claimed in claim 1 in which said sampled fluid introducing opening is in the side of the recess adjacent the bottom of the recess.

4. A sampling pipe means as claimed in claim 1 in which each fluid introducing pipe has a laterally extending portion and a turned portion on the free end thereof, and said pipe connecting block has a fluid introducing pipe opening therein opening into each recess laterally of the recess, the laterally extending portion extending through said fluid introducing pipe opening in non-contact relationship thereto and the turned portion being turned toward the bottom of said recess.

* * * * *